United States Patent [19]

Chang et al.

[11] Patent Number: 5,147,641

[45] Date of Patent: Sep. 15, 1992

[54] MICROCAPSULE FOR THE REMOVAL OF SPECIFIC AMINO ACIDS THROUGH THE ENTERO-PORTAL RECIRCULATION

[75] Inventors: Thomas M. S. Chang, St-Lambert; Louis Bourget, Pierrefonds; Colin Lister, Brossard, all of Canada

[73] Assignee: The Royal Institution for the Advancement of Learning (McGill University), Quebec, Canada

[21] Appl. No.: 719,110

[22] Filed: Jun. 24, 1991

Related U.S. Application Data

[63] Continuation of Ser. No. 327,745, Mar. 23, 1989, abandoned.

[51] Int. Cl.[5] .......................... A61K 37/48; A61K 9/50
[52] U.S. Cl. .................................... 424/94.5; 424/490; 424/491; 424/94.6
[58] Field of Search .................... 424/94.3, 94.6, 490, 424/491

[56] References Cited

PUBLICATIONS

Chang, ed., Biomedical Applications of Immobilized Enzymes and Proteins (1977), vol. I, pp. 73–76, 114.
Bourget et al., FEBS Letters, vol. 180 (1), (1985) pp. 5–8.
Edman et al., Biol. Abstracts, vol. 83 (1987) No. 74612.
Article entitled "Plasma/Intestinal Concentration Patterns Suggestive of Entero–Portal Recirculation of Amino Acids . . . " by Thomas M. S. Chang et al., Marcel Dekker, Inc. Biomat., Art. Cells, Org., 16(5) (1989) pp. 915–926.

*Primary Examiner*—Jacqueline Stone
*Attorney, Agent, or Firm*—Cushman, Darby & Cushman

[57] ABSTRACT

A microcapsule for oral administration comprising an outer layer membrane which is acid resistant and retains its structure in an alkaline environment, said membrane having dispersed therein at least one enzyme corresponding to an amino acid secreted into the intestinal or derived from a protein or peptide secreted into the intestinal tract. The present invention provides a microcapsule capable of removing specific unwanted amino acids secreted into the intestinal tract.

12 Claims, 3 Drawing Sheets

FIG. 7 — Concentration pattern of glutamine/hist after 24 hrs diet of water & sugar FIG. 8 — Concentration pattern of tyrosine 24 hrs diet of water & sugar FIG. 9 — Artificial cells immobilised asparaginase-glutaminase-tyrosinase; Ileum amino acids conc. 6 hrs after oral administration

MICROCAPSULE FOR THE REMOVAL OF SPECIFIC AMINO ACIDS THROUGH THE ENTERO-PORTAL RECIRCULATION

This is a continuation of application Ser. No. 07/327,745, filed on Mar. 23, 1989, now abandoned.

BACKGROUND OF THE INVENTION

There are several problems related to the use of enzymes and other bioreactants for therapy. These problems include immunogenicity, rapid removal, site of action, and the availibility of enzyme and bioreactants. With the advance of biotechnology, increasing number of enzymes and bioreactants can now be made available. There is therefore increasing interests to solve the other potential problems.

A number of centers have used immobilization of bioreactants to solve some of the problems mentioned (Chang, T. M. S. (ed) "Biomedical Applications of Immobilized Enzymes and Proteins" Vol. I & II, Plenum Publishing Co., New York, U.S.A., (1977); Chang, T. M. S. "Methods in the medical applications of immobilized proteins, enzymes and cells", Methods in Enzymology 137:444–457, (1988); Mosbach, K. (ed) "Immobilized Enzymes and Cells" Vol. 137 of "Methods in Enzymology", (1988); Widder, K. J. and Green, R. (ed) "Drug and Enzyme Targeting" Vol. 112 of "Methods in Enzymology" (1985)). Most of these immobilized bioreactants are used for extracorporeal blood or plasma perfusion. They are also used for parental injection especially intravenous injection. However, approaches using extracorporeal blood circulation or parental injection have their own problems. In parental injection one of the problems is related to introduction and accumulation of foreign materials in the body. The use of extracorporeal circulation (Chang, T. M. S., "Semipermeable aqueous microcapsules (Artificial cells) with emphasis on experiments in an extracorporeal shunt system., Trans. Am. Soc. Artif. Intern. Organs 12:13–19, (1966)) avoids this problem. However, it is not always easy or convenient to use extracorporeal procecures. This is especially in infants and when repeated treatments are required.

Another approach is the use of immobilized enzymes for oral administrations. Microencapsulated enzymes has been used to prevent destruction from tryptic enzymes in the intestine (Chang, T. M. S., "Artificial Cells", Charles C. Thomas Publisher, Springfield, Ill., U.S.A., (1972)). However, orally administrated enzymes have only very limited applications:

(1) use of enzyme to remove unwanted substrates from food; for example, the use of lactase to remove lactose, or phenylalanine ammonia lyase to remove phenylalanine (Bourget, and Chang, T. M. S. "Phenylalanine ammonia-lyase immobilized in semipermeable microcapsules for enzyme replacement in phenylketonuria, FEBS Letters 180:5–8, 1985);
(2) use of tryptic enzymes to supplement patients with deficiency in pancreatic secretions to allow for digestion of food;
(3) use of enzyme to remove substrates equilibrating from capillaries into the GI tract. Urea is the only one thought to equilibrate with sufficient rate across the capillaries into the intestine. Others like uric acid and creatinine are found to diffuse too slowly to be effectively removed.

In the small intestine, proteins and peptides from food are broken down into amino acids. Amino acids are then absorbed from the intestine into the portal circulation into the body. Little interest was paid to the movement of amino acids from the body into the intestine. Most authors assume that these movements are by passive diffusion or other membrane transport mechanisms. These proposals are mainly based on studies using isolated intestinal segments or brush border membrane vesicles (Christensen, H. N., Feldman, B. H. and Hastings, A. B., "Contractive and reversible character of intestinal amino acid transport", Am. J. Physiol 205(2) 255-260 (1963); Bertellot, A., Malo, C. "Maladies membranaires de l'intestin et du rein", Medicine/sciences I:427–434 (1985); Bertellot, A., Khan, A. H., Ramaswamy, K., "K and Na gradient dependent transport of L-phenylalanine by mouse intestinal brush border membrane vesicles" Biochmi. Biophys. Acta 691:321-331 (1982); Cooke, H. J., Fankuche, L., Cooke, A. R. "Tryptophan transport by isolated newborn rabbit jejunum" The American Physiology Society 239: G306-G310 (1980); Samiy, A. H., Spencer, R. P. "Accumulation of L-phenylalanine by segments of small intestine" Am. J. Physiol. 200(3): 505-507 (1961)).

It is known that proteins and peptides are secreted into the intestinal tract. However, no studies were carried out on the extent of contribution of this to the amino acid sources.

SUMMARY OF THE INVENTION

Surprisingly and in accordance with the present invention there is provided a method for the specific depletion of body amino acids by oral ingestion of bioreactants like immobilized enzymes.

The method of the present invention provides an improvement over the prior art. Since, it provides a mean for oral administration of bioreactants which can selectively remove specific amino acids from the body. This prevent the problems related to injection, like for example accumulation, toxicity, immunological and allergic reactions. It also prevents the problems related to extracorporeal circulation, like clotting, adverse effects on blood cells, embolism and the need for invasive vascular access. Any bioreactants could be given to selectively remove specific amino acids from the body.

Asparaginase could be given parentally for the treatment of leukemia in combination with other drugs (Clavell et al., New Drug J. Med. 315: pgs. 657-663, 1986). Injection of asparaginase increased survival rate, but caused problems like allergic reactions, toxicity, hemorrage, strokes and so on.

Also in accordance with the present invention, immobilized asparaginase can be administered orally instead of being injected. Therefore, it would prevent the patient from having all the side effects related to the injection of the enzyme.

In inborn errors of metabolism due to an enzyme deficiency, where there is an increase in tyrosine and other amino acids levels. In accordance with the present invention, immobilised enzyme like tyrosinase can be given orally instead of being injected repeatedly into the infant with all the side effects.

This study suggests the presence of an entero-portal recirculation of a very large amount of amino acids. Endogenous sources of amino acids are secreted at high concentration into the small intestine. Most of the amino acids are absorbed as the content passes down the small intestine. Plasma amino acid concentrations are on the average only 1-5% of the concentrations in the duodenum.

Furthermore, the present invention provides a method for the removal of unwanted amino acids from the body which comprises, administering orally a microcapsule consisting of an outer layer membrane which is acid resistant and retains its structure in an alkaline environment, the membrane having dispersed therein at least one enzyme or one bioreactant corresponding to an amino acid secreted into the intestinal tract or derived from a protein or a peptide secreted into the intestinal tract.

EXAMPLES OF PROTEINS AND PEPTIDES IN SMALL INTESTINE NOT DERIVED FROM FOOD

1) Stomach Secretions Entering Intestine mucus
mucins- glycoprotein (rich in threonine, serine, proline, also cystine)
pepsin
pepsinogen
gastrin

2) Pancreatic Secretions into Intestine trypsin
chymotrypsin
carboxypeptidase
deoxyribonuclease
ribonuclease
elastase
lipase
amylase
hydrolase
phospholipase
vasoactive intestinal polypeptides

3) Intestinal Wall Secretions mucus
enterokinase
secretion
cholecystokinin
aminopeptidases
dipeptidases
dipeptidyl aminopeptidase

4) Peptides From Breakdown of Protein in Stomach and Intestine dipeptides
tripeptides
tetrapeptides
oligopeptides This is true even in rats on 24 hours of water and sugar with no exogenous sources of amino acids. For example, in rats free from exogenous sources of amino acids, the PLASMA:DUODENUM concentrations ($\mu$mole/liter) are: Asparagine 37:7164, Tyrosine 94:9579, and glutamine/histidine 409:9708. This result for the first time shows that 80-85% of the amino acids in the small intestine, come from endogenous sources, and not from food. This entero-portal recirculation of very large amounts of exogenous amino acids means the potential of a method for specific depletion of body amino acids by oral ingestion of bioreactants like immobilized enzymes. Preliminary studies used artificial cells to immobilize asparaginase, glutaminase and tyrosinase by microencapsulation. Six hours after 1 oral administration, asparagine, glutamine and tyrosine in the ileum were lowered to 10% of the level of the control. Artificial cells containing no enzymes were used as the control.

DETAILED DESCRIPTION OF THE INVENTION

The reasoning of the present invention is as follows:
1. The pattern of amino acid concentrations in the gastrointestinal tract and plasma in animals on normal diet would depend on exogenous sources of amino acids. This could be very variable and difficult to analyse.
2. If we eliminate amino acid sources from ingestion for 24 hours, this would exclude exogenous sources of amino acids in the intestinal tract. This should give us a much clearer picture of the mechanisms of movement of amino acids across the intestinal tract without interference from exogenous sources.
3. Having obtained the baseline in 2 above, one can then study the effect of oral administration of artificial cells containing asparaginase, glutaminase and tyrosinase.

Figure 1:
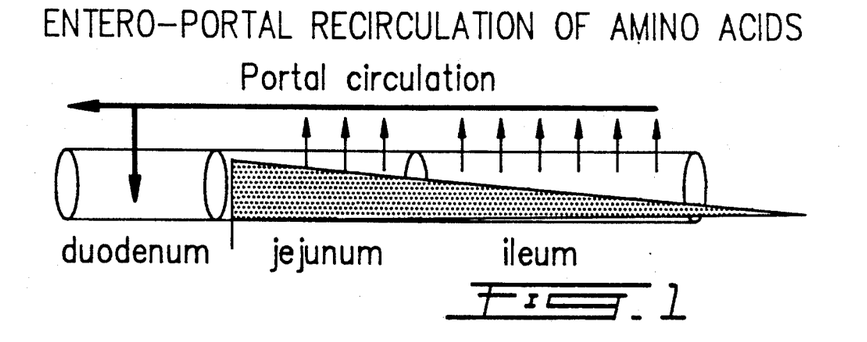
FIG. 1 shows the entero-portal recirculation of amino acids.
Figure 2:
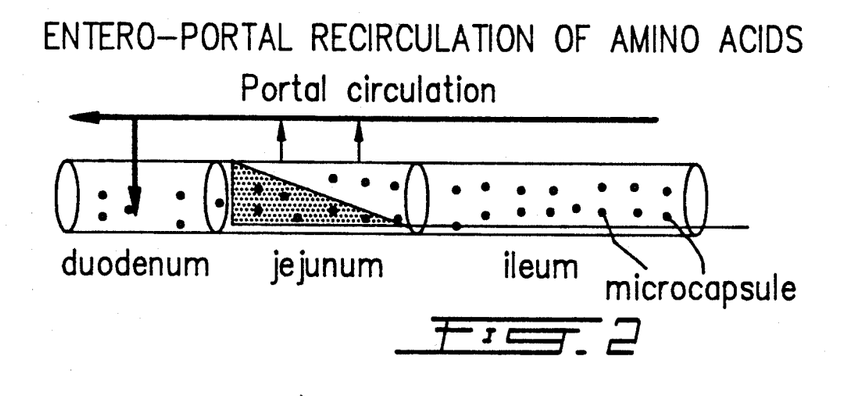
FIG. 2 shows the microcapsule used to remove specific amino acids through the entero-portal recirculation of amino acids.

The results obtained strongly suggest the presence of an enteroportal recirculation of a very large amount of amino acids (FIG. 1). The present study shows that endogenous sources of amino acids are secreted at high concentration into the small intestine. Most of the amino acids are absorbed as the content passes down the small intestine. Previous to the present report, the only material which follows this pattern are bile salts which are secreted in the bile. However, in the rats, the amino acids studied in the present experiment do not come from biliary section. This new finding of the presence of a entero-portal recirculation of a very large amount of amino acids means that we may have the basis of a useful method. A method for specific depletion of body amino acids by oral ingestion of bioreactants like immobilized enzymes (FIG. 2). Preliminary studies shown here indicate that this is possible. Thus, one oral dose of artificial cells containing asparaginase, tyrosinase and glutaminase selectively lowered the corresponding three amino acid throughout the small intestine. This prevents these amino acids from reentering the body. The concentration of amino acids in the small intestine is generally 100 times higher than that in the plasma. Thus repeated long term administration of selected bioreactants would result in depleting the specific substrate from the body. This is done by removing the specific amino acids in the small intestine and preventing their entero-portal recirculation. This holds potentials for the selective depletion of specific body amino acids. One example is the use of asparaginase and glutamine for the depletion of asparagine and glutamine in tumour therapy. Another example is the depletion of tyrosine in enzyme deficiency diseases with accumulation of this amino acids. The oral administration approach is applicable to those situations where the amino acids and other substances can be removed from the body fluids. Other substances in the body which follow this pattern of entero-portal recirculation can also be selectively depleted through oral administration of specific bioreactants. However, there are other situations, as in storage diseases where this approach is not applicable.

Analysis of amino acid concentrations in plasma, stomach, duodenum, jejunum and ileum. This is based on a slight modification of the High Performance Liquid Chromatography method of Hill et al (Hill, D. W., Walker, F. H., Wilson T. D., Stuard, J. D.; "High performance liquid chromatography determination of amino acids in the pico-mole range", Analytical Chemistry 51:(8) 1338–1341 (1979)).

Experimental animals Sprague Dawley rats weighing between 275 to 330 grams were obtained from Charles River Co., St. Constant, Quebec.

EXPERIMENTAL DESIGN

Procedure of Preparation

Reagents

Hemoglobin solution: 15 g of hemoglobin (Sigma bovine hemoglobin type 1, 2× crystallized, dialyzed, and lyophillized) is dissolved in 100 ml of distilled water, then filtered through Whatman No. 42 filter paper. The final concentration of hemoglobin in the filtrate is adjusted to 10 g/100 ml.

Enzyme solutions: Enzymes (single, multiple, insolubilized, cell extract or other material) are dissolved or suspended in the hemoglobin solution. Suitable adjustment is required to maintain a final concentration of 10 g of hemoglobin per 100 ml. Also, a minimum pH of 8.5 should be maintained by the use of Tris buffer.

Organic solution: 100 ml. of ether (analytical grade) is saturated with water by shaking with distilled water in a separating funnel, then discarding the water layer.

Cellulose nitrate solution: This is prepared by evaporating to completely dry 100 ml of collodion (USP, 4 g of cellulose nitrate in a 100-ml mixture of one part alcohol and three parts ether) into a thin sheet, then dissolving to its original volume by using a solution consisting of 82.5 ml of ether and 17.5 ml of alcohol. This exact composition is important for membrane formation.

n-Butyl benzoate (Eastman)

Tween-20 solutions: 50% Tween 20 ® solution is prepared by dissolving 50 ml of Tween 20 ®, an oil-/water emulsifying agent (Atlas Powder Company, Canada Ltd., Montreal, Quebec, Canada) in an equal volume of distilled water, 1% Tween 20 ® solution is prepared by dissolving 1 ml of Tween 20 ® in 99 ml of water. The pH in both solutions should be adjusted using buffer to 7.

Magnetic stirrer: It is important to have a magnetic stirrer with sufficient power to give the speed (rmp) stated, especially when stirring the very viscous Tween 20 mixture. The Jumbo Magnetic Stirrer (Fisher Scientific Company, Montreal, Quebec, Canada) is used in the procedures described below. Also needed is a 4-cm magnetic stirring bar and a 150-ml glass breaker with an internal diameter of less than 6 cm.

Procedure

All procedures are carried out at 4°. To a 150-ml glass beaker containing 2.5 ml of Tris-buffered hemoglobin solution (containing the enzymes to be included), add 25 ml of the organic solution. The mixture is immediately stirred with the magnetic stirrer at a speed setting of 5 (1200 rpm). After stirring for 5 sec, 25 ml of the cellulose nitrate solution is added and stirring is continued for another 60 sec. The beaker is then covered and allowed to stand unstirred at 4° for 45 min.

The microcapsules should be completely sedimented by the end of 45 min. Decant most of the supernatant. Immediately add 30 ml of the n-butyl benzoate to the beaker and stir at a speed setting of 5 for 30 sec. The beaker is then allowed to stand uncovered and unstirred at 4° for 30 min.

The final step is to transfer the microencapsulated enzyme from the organic liquid phase into an aqueous phase. First, butyl benzoate supernatant should be removed completely. In the case where microcapsules greater than 50 μm in diameter are prepared, this can be done readily if the microcapsules have sedimented completely by 30 min. If the microcapsules have not sedimented completely, then centrifugation at 350 g for 5 min is required.

After removal of supernatant, 25 ml of the 50% Tween 20 ® solution is added. The suspension is immediately dispersed by stirring with the Jumbo Magnetic Stirrer at a speed setting of 5 for 30 sec, and then 25 ml of water is added. After a further 30 sec of stirring, the suspension is further diluted with 200 ml of water. The slightly lurbid supernatant may now be removed by centrifugation of the suspension at 350 g for 5 min.

The microencapsulated enzymes so obtained are washed repeatedly in 1% Tween 20 ® solution until no further leakage of hemoglobin takes place and the smell of butyl benzoate is no longer detectable. The removal of n-butyl benzoate with 1% Tween ® solution is very important because, unless it is completely removed, butyl benzoate may affect the permeability characteristics of the semipermeable microcapsules.

The final preparation is suspended in a solution containing 0.9 g sodium chloride per 100 ml of water or in a suitable buffer solution. This is not a difficult procedure if the exact concentrations, timing, material, and other steps, are followed exactly as described. Omissions or modification, even extremely minor, may result in a great deal of problems requiring extensive readjustment. It is suggested that the exact procedure be followed at first. Modifications should be carried out after the procedure has been repeated well enough to result in good artificial cells.

The rats were divided into three groups:
1. First group of rats were maintained on standard rat diet and water ad libitum. Samples were taken from amino acid analysis.
2. Second group of rats were maintained the same way as above. However, 24 hours before sampling for amino acids they were placed on a diet consisting of sugar cubes and water ad libitum. Faeces were allowed to drop through the metabolic cages to exclude all potential exogenous amino acid sources during the 24 hours period.
3. Artificial cells containing asparaginase, glutaminase and tyrosinase were given orally via a stomach tube. This was given after 24 hours on the sugar water diet. Six hours after the administration of artificial cells, samples were taken for analysis of amino acids. As control, artificial cells without the three enzymes were also given in the same way.

After the animals were sacrificed samples were immediately taken from plasma, duodenum, jejunum and ileum and kept frozen until use. For Groups 2 and 3, samples from the stomach were also taken to make sure there were no exogenous source of amino acids. Detailed measurements and statistical analysis were carried out for group 1 and 2. Detailed analysis for all amino acids were carried out.

Artificial Cells Immobilized Asparaginase, Glutaminase and Tyrosinase

These were prepared using a modified form (Chang, T. M. S. "Recycling of NAD(P) by multienzyme systems immobilized by microencapsulation in Artificial Cells" Methods in Enzymology 136:67-82, (1987)) of the original microencapsulation procedure (Chang, T. M. S., "Semipermeable Microcapsules", Science 146:525—525, (1964)) based on cellulose nitrate (collodion) membranes. Each ml of artificial cells contained 100 units of Asparaginase, 5 units of Glutaminase and 2,000 units of Tyrosinase. The enzymes were obtained from Sigma Co. Asparaginase (EC 3.5.1.1) was Grade VIII from $E.$ $coli$, chromatographically purified, lyophilized powder, with activity of 200-300 units per mg protein, Glutaminase (EC 3.5.1.2) was Grade V from $E.$ $coli$, lyophilized soluble powder with activity of 50-200 units per mg protein. Tyrosinase (EC 1.14.18.1) was from Mushroom with activity of 2,000-4,000 units per mg. The artificial cells were suspended in saline as a 25% suspension for administered by a stomach tube through a syringe. Control artificial cells were also prepared in exactly the same way except that the three enzymes were not included.

Plasma/Intestinal Concentration Pattern of Amino Acids of Rats on Normal Diet

All amino acids show a general pattern. The concentration of amino acids in the duodenum section of the small intestine is generally 100 times higher than that in the plasma. This is the case for alanine, arginine, asparagine, aspartic acid, glutamine/histidine, glutamic acid, hydroxyproline, isoleucine, leucine, lysine, methiopine, Ornithine, phenylalanine, serine, taurine, threonine, tryptophan, tyrosine, and valine. On the whole, most amino acids concentrations are the highest in the duodenum and decreasing down the small intestine in the jejunum and lowest in the ileum. However, even in the ileum the concentrations are higher than those in the plasma.

TABLE 1

| Amino Acids | plasma ctrl | plasma fasted | stomach fasted | duod. ctrl | duod. fasted | jejen. ctrl | jejen. fasted | ileum ctrl | ileum fasted |
|---|---|---|---|---|---|---|---|---|---|
| asp | 15 | 17 | ERR | 10912 | 4935 | 4643 | 3053 | 2298 | 1996 |
| glu | 235 | 300 | 1344 | 24558 | 20131 | 13922 | 16302 | 8125 | 6784 |
| asn | 57 | 37 | 17 | 9459 | 7164 | 4621 | 4907 | 2488 | 1728 |
| ser | 218 | 135 | 358 | 18796 | 13313 | 7838 | 5864 | 3811 | 2159 |
| his/gln | 598 | 409 | 133 | 10848 | 9708 | 4832 | 5421 | 1879 | 1905 |
| gly | 331 | 101 | 621 | 15206 | 9766 | 8964 | 13069 | 7906 | 7712 |
| thr | 291 | 146 | 426 | 14294 | 11139 | 6407 | 6892 | 3503 | 2627 |
| arg | 118 | 46 | 99 | 18423 | 15032 | 10182 | 6750 | 1966 | 1464 |
| ala | 420 | 425 | 1348 | 26813 | 25462 | 11743 | 14159 | 5789 | 5036 |
| gaba | 0 | 0 | 39 | 0 | 0 | 0 | 0 | 0 | 0 |
| tau | 187 | 110 | 678 | 4988 | 4688 | 5049 | 6673 | 5493 | 7253 |
| tyr | 92 | 94 | 390 | 5288 | 9579 | 3898 | 6366 | 1913 | 1767 |
| aaba | 0 | 0 | 102 | 2348 | 0 | 0 | 0 | 0 | 0 |
| val | 250 | 105 | 635 | 20868 | 17301 | 8577 | 9610 | 4151 | 3584 |
| met | 68 | 49 | 143 | 8568 | 7705 | 3188 | 4304 | 1241 | 1190 |
| hyl | 29 | 4 | 85 | 1462 | 928 | 1144 | 1345 | 656 | 443 |
| trp | 68 | 56 | 42 | 3748 | 3330 | 1608 | 1875 | 700 | 549 |
| ileu | 117 | 65 | 442 | 17063 | 15339 | 6945 | 9007 | 2982 | 3112 |
| phe | 111 | 63 | 448 | 14319 | 13377 | 5516 | 7282 | 2389 | 2060 |
| leu | 205 | 106 | 933 | 34726 | 31892 | 12728 | 17494 | 5210 | 5026 |
| eth | 0 | 0 | 0 | 0 | 0 | 0 | 0 | 0 | 0 |
| orn | 78 | 0 | 599 | 609 | 207 | 0 | 0 | 0 | 0 |
| lys | 418 | 88 | 699 | 22186 | 16291 | 8534 | 8026 | 3598 | 1688 |

| Amino Acids | serum fasted | stomach fasted | duod. fasted | jejen. fasted | ileum fasted | large intestine fasted |
|---|---|---|---|---|---|---|
| chol | 39.2 | 4.32 | 84.2 | 29.4 | 45.3 | 42 |
| t bil | 0.19 | 0.92 | 1.84 | 5.69 | 13.71 | 5.16 |
| urea N | 6.05 | 23.41 | 47.97 | 25.59 | 26.23 | 45.13 |

Figure 3:
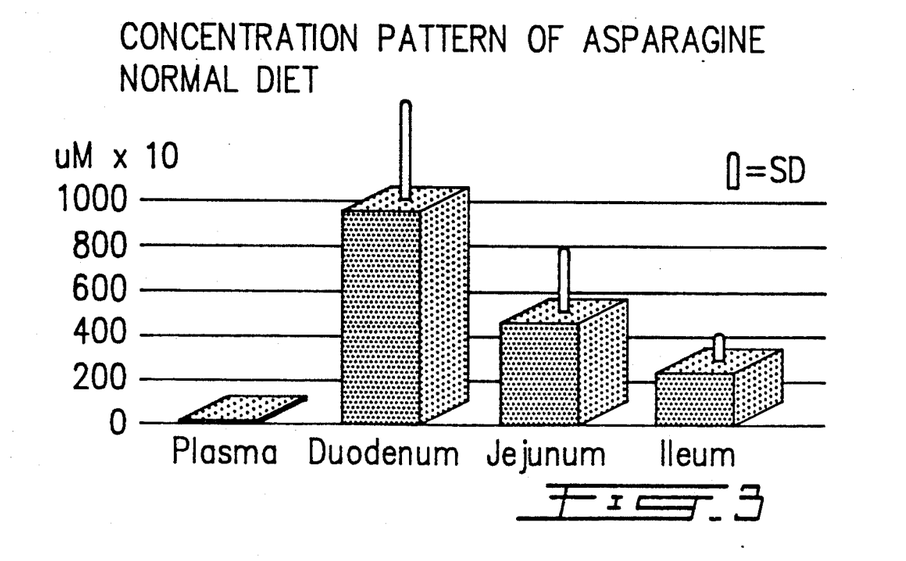
FIG. 3 shows the concentration pattern of asparaginase in plasma, duodenum, jejunum and ileum of rats on normal diet (means and standard deviations).
Figure 4:
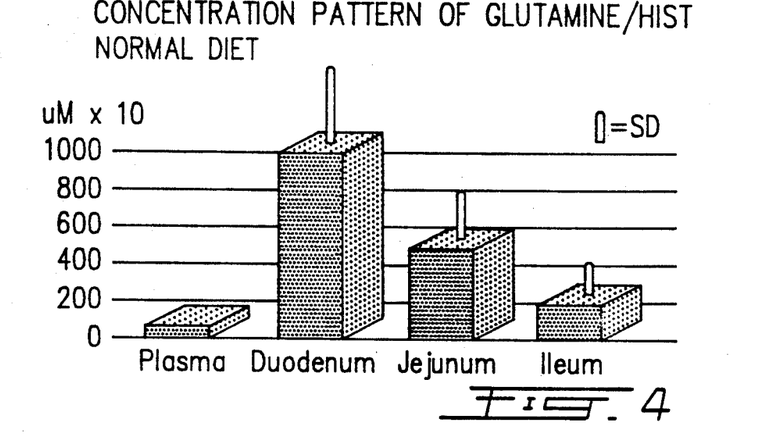
FIG. 4 shows the concentration pattern of glutamine/histidine in plasma, duodenum, jejunum and ileum of rats on normal diet (means and standard deviations).
Figure 5:
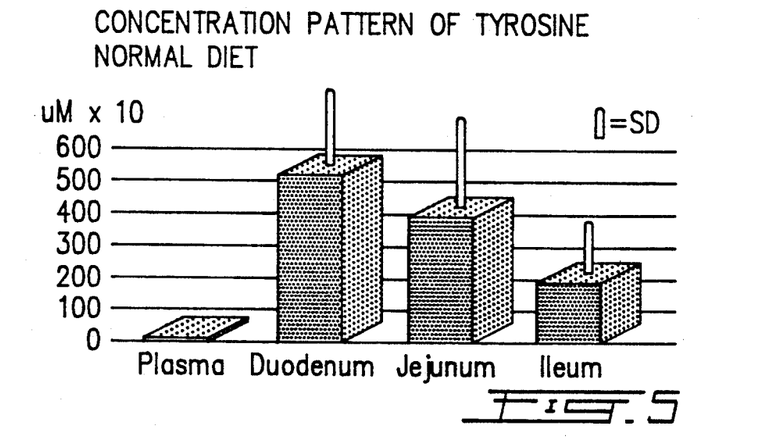
FIG. 5 shows the concentration pattern of tyrosine in plasma, duodenum, jejunum and ileum of rats on normal diet (means and standard deviations).

FIGS. 3, 4 and 5 show the results obtained for asparagine, tyrosine and glutamine/histidine. The present HPLC methods does not separate glutamine from histidine. The mean concentration of plasma asparagine is 57 $\mu$mole/liter compared to 9,459 $\mu$mole/liter in the duodenum. The mean concentration of plasma tyrosine is 92 $\mu$mole/liter in the plasma compared to 5,228 $\mu$mole/- liter in the duodenum. The mean concentration of plasma glutamine/histidine is 598 μmole/liter compared to 10,848 μmole/liter in the duodenum.

The concentration decreases as one moves down the small intestine to the jejunum and the ileum. The standard explanation for this is that exogenous sources of amino acids from food are digested in the small intestine. This is why there is such a high concentration of amino acids as compared to the plasma. As the intestinal contents travel down the small intestine, amino acids are absorbed resulting in a decreasing concentration. If this plasma/intestinal concentration pattern is due to exogenous sources of amino acids, then we should see a different pattern in the absence of exogenous sources. The next experiment is carried out to answer this question.

Figure 6:
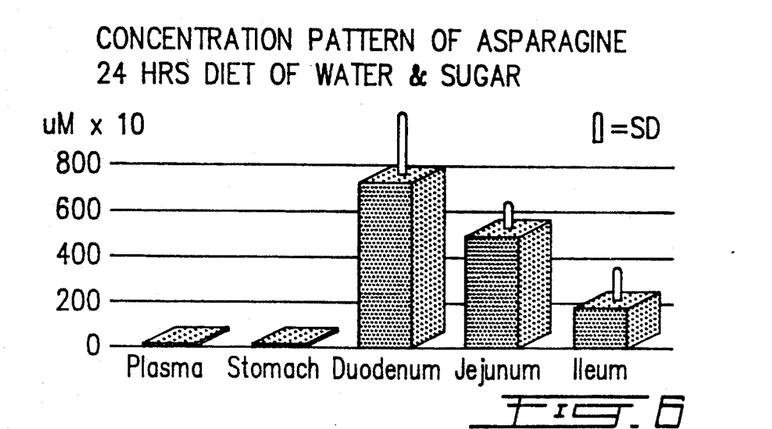
FIG. 6 shows the concentration pattern of asparaginase in plasma stomach, duodenum, jejunum and ileum of rats after 24 hours of diet free of amino acid sources (means and standard deviations).
Figure 7:
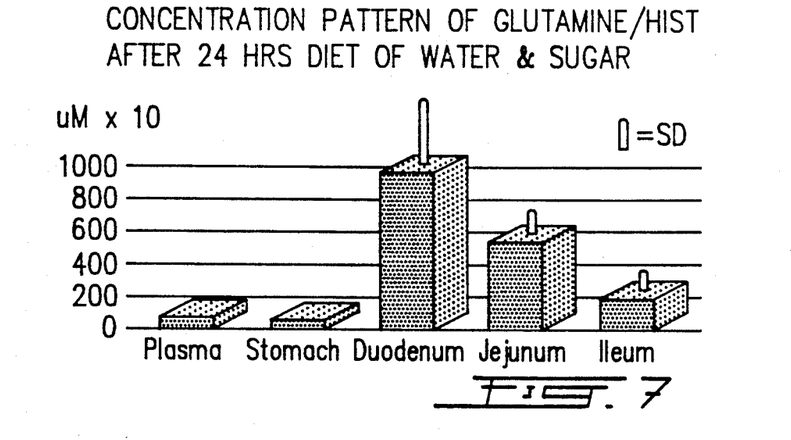
FIG. 7 shows the concentration pattern of glutamine/histidine in plasma stomach, duodenum, jejunum and ileum of rats after 24 hours of diet free of amino acid sources (means and standard deviations).
Figure 8:
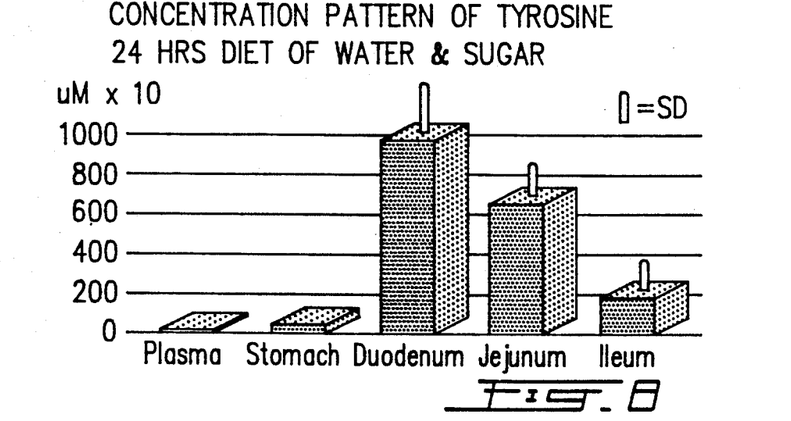
FIG. 8 shows the concentration pattern of tyrosine in plasma stomach, duodenum, jejunum and ileum of rats after 24 hours of diet free of amino acid sources (means and standard deviations).
Figure 9:
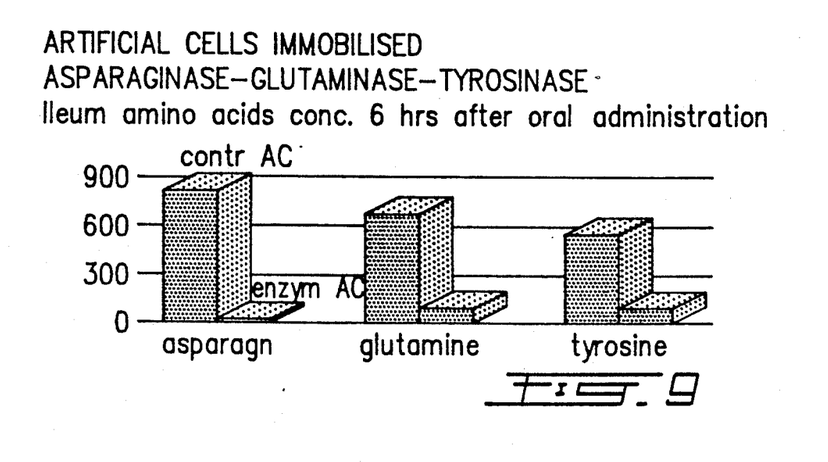
FIG. 9 shows the effects of oral administration of artificial cells containing asparaginase, glutaminase and tyrosinase (enzyme AC) and control artificial cells containing no enzymes (contr AC) on amino acid concentrations in ileum.

Plasma/Intestinal Concentration Pattern of Amino Acids of Rats on 24 Hours Diet with No Exogenous Sources of Amino Acids FIGS. 6, 7 and 8 summarized the results obtained. The concentration of asparagine, glutamine/histidine, tyrosine and other amino acids showed negligible level of amino acids in the stomach. The plasma concentration of amino acids is not significantly different from those of rats on regular diet. What is most surprising is that the plasma/intestinal concentration pattern of amino acids of this group of rats is similar to those on normal diet. Furthermore, the amino acid concentrations are still highest in the duodenum, and decreasing as the contents move down to the jejunum and ileum.

The mean concentration of asparagine in the plasma is 37 μmole/liter compared to the duodenum mean concentration of 7,164 μmole/liter. The mean concentration of tyrosine in the plasma is 94 μmole/liter compared to the duodenum concentration of 9,579 μmole/liter. The mean concentration of glutamine/histidine in the plasma is 409 μmole/liter compared to the duodenum mean concentration of 9,708 μmole/liter. As far as we know, this is the first demonstration of such a high concentration of amino acids in the absence of exogenous sources. The mean concentrations also decrease down the small intestine in a pattern similar to that of the rats on standard diet. The very high duodenum/plasma ratio is not due to concentration effects from the removal of water. Simultaneous measurements of urea nitrogen showed no significant differences between urea nitrogen in the plasma and duodenum. These results seem to indicate that a major part of the amino acids in the small intestine of the rats come from endogenous sources. This may be in the form of secretions into the small intestine, especially in the duodenum. In the rat this does not come from biliary secretion. Asparagine, glutamine and tyrosine concentrations in the bile of rats is in the same order of concentration as in the plasm (Folsch, U. R., and Wormsley, K. G., "The amino acid composition of rat bile", Experientia 33:1055–1056 (1977)). It is likely that endogenous protein and peptide secretion from stomach, pancreatic secretion and internal glandular secretions contribute to this high amino acid level. Attached is a list of some examples of proteins and peptides from endogenous sources. This is not an exhaustive list since there are many others.

These observations seem to suggest the presence of an entero-portal recirculation of a very large amount of amino acids. Up to now, it has been known that there is such a high level and large amount of endogenous sources of amino acids in their type of entero-portal recirculation. Endogenous sources of amino acids are secreted at high concentration into the duodenum. Most of the amino acids are absorbed as the content passes down the small intestine. This novel finding of entero-portal recirculation of very large amounts of amino acids would allow for a very useful method. A mean for specific depletion of body amino acids resulted from oral ingestion of bioreactants like immobilized enzymes. To test this possibility, the next study was carried out.

Plasma/Intestinal Amino Acid Patterns After 24 Hours Amino Acid Free Diet and 6 Hours After Oral Administration of Asparaginase-Glutaminase-Tyrosinase Artificial Cells After 24 hours on the sugar and water diet, artificial cells containing asparaginase, glutaminase and tyrosinase were given orally in one dose. 6 hours later amino acid concentrations were measured. The only marked lowering in amino acid concentrations were observed for asparagine, tyrosine and glutamine. Their concentrations in the duodenum, jejunum and ileum are all lower than the control group on sugar and water diet. This is most marked in asparagine.

TABLE 2

| Amino Acids | Plasma | Duodenum | Jejunum | Ileum | Stomach |
|---|---|---|---|---|---|
| WATER AND SUGAR DIET PLUS MICROCAPSULES CONTAINING ASPARAGINASE, GLUTAMINASE AND TYROSINASE | | | | | |
| asp | 64.88541 | 8434.972 | 5373.400 | 2463.382 | 273.2526 |
| glu | 235.2508 | 17089.87 | 12877.01 | 5028.120 | 2101.921 |
| asn | 76.87468 | 5092.676 | 2020.698 | 214.3947 | 0 |
| ser | 344.4512 | 13998.78 | 4668.717 | 1371.738 | 2700.544 |
| his/gln | 553.0046 | 6938.278 | 3516.016 | 845.3524 | 289.3229 |
| gly | 289.0008 | 15821.32 | 25642.70 | 7780.907 | 2051.688 |
| thr | 522.7523 | 9614.452 | 5556.633 | 1442.330 | 1660.138 |
| arg | 198.0833 | 12426.35 | 4707.466 | 445.3173 | 0 |
| ala | 543.1531 | 21665.42 | 12194.92 | 3022.992 | 4573.228 |
| gaba | 0 | 226.4086 | 0 | 0 | 0 |
| tau | 369.4076 | 9813.805 | 29576.86 | 9441.852 | 1157.794 |
| tyr | 110.7968 | 6994.986 | 3742.598 | 325.1571 | 928.3778 |
| aaba | 8.783220 | 8371.190 | 96.72383 | 0 | 72.75938 |
| val | 252.9842 | 5187.258 | 7604.836 | 2894.568 | 2771.457 |
| met | 64.96956 | 679.8259 | 2775.944 | 77.74914 | 768.1192 |
| hyl | 27.93910 | ERR | 1158.751 | 152.6808 | 225.0732 |
| trp | 106.7357 | 2319.370 | 1255.034 | 433.4839 | 275.7370 |
| ileu | 114.0508 | 10428.09 | 6028.469 | 1370.091 | 904.8293 |
| phe | 154.5171 | 10252.63 | 4555.397 | 1467.439 | 2170.196 |
| leu | 228.3732 | 24886.49 | 11155.38 | 3194.576 | 2796.127 |
| eth | 0 | 0 | 0 | 0 | 0 |

TABLE 2-continued

| Amino Acids | Plasma | Duodenum | Jejunum | Ileum | Stomach |
|---|---|---|---|---|---|
| orn | 37.51628 | 749.3745 | 153.8877 | 0 | 2247.269 |
| lys | 331.6141 | 16413.21 | 5691.431 | 405.9942 | 3371.676 |
| WATER AND SUGAR DIET PLUS MICROCAPSULES CONTAINING NO ENZYME | | | | | |
| asp | 38.90193 | 13549.73 | 7922.320 | 9524.659 | 61.94660 |
| glu | 227.6594 | 30768.31 | 16570.32 | 21091.40 | 324.3381 |
| asn | 74.47742 | 11478.94 | 5293.902 | 8211.039 | 24.37466 |
| ser | 280.0234 | 25881.82 | 8035.004 | 13709.64 | 306.7981 |
| his/gln | 579.9798 | 12721.72 | 4722.411 | 6605.306 | 116.7981 |
| gly | 436.9091 | 21194.51 | 11720.74 | 14301.07 | 516.8357 |
| thr | 401.2572 | 18390.92 | 8098.428 | 11243.36 | 316.5980 |
| arg | 155.6900 | 22667.74 | 5455.052 | 11659.72 | 7.565737 |
| ala | 568.6544 | 38053.69 | 14146.97 | 20055.39 | 1030.555 |
| gaba | 0 | 0 | 0 | 0 | 214.8060 |
| tau | 416.7733 | 5189.431 | 14292.98 | 6645.600 | 580.5902 |
| tyr | 97.88015 | 6325.310 | 4618.760 | 5366.220 | 218.8960 |
| aaba | 6.631754 | 0 | 0 | 0 | 14.87592 |
| val | 235.1828 | 26575.60 | 10027.35 | 14954.70 | 491.2305 |
| met | 79.92534 | 10736.00 | 3282.394 | 5382.590 | 136.9020 |
| hyl | 55.44666 | 1597.619 | 1807.960 | 1584.936 | 79.46667 |
| trp | 70.62977 | 4822.134 | 1496.829 | 3008.815 | 47.52178 |
| ileu | 119.5205 | 22414.55 | 7719.330 | 12151.03 | 122.8996 |
| phe | 114.4726 | 17422.23 | 5507.631 | 9332.477 | 590.8442 |
| leu | 225.1433 | 45050.67 | 14019.44 | 21467.87 | 959.1661 |
| eth | 0 | 0 | 0 | 0 | 0 |
| ern | 53.33728 | 1045.781 | 814.9832 | 469.1555 | 356.0537 |
| lys | 471.7707 | 32455.54 | 4381.274 | 13287.65 | 162.1255 |

The results comparing enzyme-artificial cells and control artificial cells are shown in FIG. 7. This result is obtained 6 hours after one oral administration. This result shows that immobilized enzymes are effective in removing amino acids in the small intestine.

There are different possible types of bioreactants:

1. 4 Types of Immobilised Enzymes 1) microencapsulated enzymes with a high concentration of enzyme protected from intestinal digestive enzymes amino acid which can diffuse into the microcapsule,
2) other immobilized enzyme system
   a) Adsorbed wherein enzymes are not protected from digestive enzymes
   b) covalent linkage wherein the enzymes are not protected from the digestive enzymes
   c) matrix entrap wherein only a small amount of enzymes possible;

2. Specific adsorbents which can remove specific amino acids;
3. Microcapsulation or matrix entrapment of:
   a) microorganisms (e.g. bacteria) which can convert, metabolise or remove specific amino acids
   b) cell cultures which can convert, metabolise or remove specific amino acids;
4. Other materials which can remove specific amino acids.

We claim:

1. A method for decreasing the reabsorption of at least one undesirable endogenous amino acid selected from only the amino acids secreted directly into the intestinal tract from the enteroportal recirculation system of the human body, which comprises orally administering microcapsules consisting of an outer-layer membrane which is acid resistant and retains its structure in an alkaline environment, said membrane encapsulating at least one enzyme capable of degrading said undesirable amino acid present in the intestinal tract or derived from a protein or peptide secreted into the intestinal tract wherein said undesirable amino acid in the intestinal tract will diffuse into said microcapsules where said amino acid is subjected to a partial or complete degradation by the encapsulated enzyme and the degradation products are then secreted from said microcapsules into the intestinal tract and said microcapsules are naturally excreted from the intestinal tract.

2. The method of claim 1, wherein the enzyme is asparaginase and the secreted amino acid is asparagine.

3. The method of claim 1, wherein the enzyme is tyrosinase and the secreted amino acid is tyrosine.

4. The method of claim 1, wherein the enzyme is glutaminase and the secreted amino acid is glutamine.

5. The method of claim 1, wherein the enzyme is histidinase and the secreted amino acid is histidine.

6. The method of claim 1, wherein the enzyme is tryptophanase and the secreted amino acid is tryptophan.

7. The method of claim 1, wherein the enzyme is phenylalanine ammonialyase and the secreted amino acid is valine.

8. The method of claim 1, wherein the enzyme is arginase and the secreted amino acid is arginine.

9. The method of claim 1, wherein the enzyme is lysine decarboxylase and the secreted amino acid is lysine.

10. The method of claim 1, wherein the enzyme is methionine racemase and the secreted amino acid is methionine.

11. The method of claim 1, wherein the enzyme is cystine desulphydrase and the secreted amino acid is cystine.

12. The method of claim 1, wherein the enzyme is a deaminase and the secreted amino acid is proline.

* * * * *

UNITED STATES PATENT AND TRADEMARK OFFICE
CERTIFICATE OF CORRECTION

PATENT NO. : 5,147,641
DATED : September 15, 1992
INVENTOR(S) : Chang et al.

It is certified that error appears in the above-identified patent and that said Letters Patent is hereby corrected as shown below:

Col. 12, line 50, "valine" should be --phenylalanine--.

Signed and Sealed this

Seventeenth Day of December, 1996

Attest:

BRUCE LEHMAN

Attesting Officer  Commissioner of Patents and Trademarks